United States Patent [19]
Naito et al.

[11] Patent Number: 5,476,649
[45] Date of Patent: Dec. 19, 1995

[54] HAIR COSMETIC COMPOSITION

[75] Inventors: Sachio Naito, Ichikaimachi; Keiko Taketomi, Utsunomiya; Koji Yoshino, Utsunomiya; Kouji Morita, Funabashi; Junichi Sugita, Miyashiro; Kazuyuki Yahagi, Tokyo, all of Japan

[73] Assignee: Kao Corporation, Tokyo, Japan

[21] Appl. No.: 785,932

[22] Filed: Oct. 31, 1991

[30] Foreign Application Priority Data

Nov. 2, 1990 [JP] Japan ..................... 2-298037

[51] Int. Cl.$^6$ ..................................... A61K 7/06
[52] U.S. Cl. .................. 424/70.1; 424/401; 514/785
[58] Field of Search ............... 424/70, 71, 70.1, 424/401, 70.11, 70.12, 70.27, 70.28, 70.31; 514/785, 786, 784

[56] References Cited

U.S. PATENT DOCUMENTS

| | | | |
|---|---|---|---|
| 4,371,469 | 2/1983 | Foglia et al. | 554/161 |
| 4,464,272 | 8/1984 | Parslow et al. | 252/8.8 |
| 4,464,273 | 8/1984 | Parslow et al. | 252/8.8 |
| 4,490,280 | 12/1984 | Joshi et al. | 252/368 |
| 4,597,964 | 7/1986 | Ziemelis et al. | 424/70 |
| 4,673,571 | 6/1987 | Mahieu et al. | 424/70 |
| 4,711,776 | 12/1987 | Suzuki et al. | 424/70 |
| 4,740,432 | 4/1988 | Bosserelle | 424/70 X |
| 4,859,457 | 8/1989 | Suzuki et al. | 424/70 |
| 4,985,466 | 1/1991 | Deguchi | 514/724 |
| 5,011,680 | 4/1991 | Suzuki et al. | 424/64 |
| 5,037,564 | 8/1991 | Nishizaki et al. | 252/22 |
| 5,051,251 | 9/1991 | Morita et al. | 424/70 |
| 5,080,889 | 1/1992 | Katada et al. | 424/70 X |
| 5,219,733 | 6/1993 | Myojo et al. | 435/52 |

FOREIGN PATENT DOCUMENTS

| | | |
|---|---|---|
| 0134998 | 3/1985 | European Pat. Off. . |
| 0204586 | 12/1986 | European Pat. Off. . |
| 0391431 | 10/1990 | European Pat. Off. . |
| 2558154 | 7/1985 | France . |

OTHER PUBLICATIONS

CA 88:37026f, "Thermodynamic . . . indexes" Chem. Abstracts, Golovnya et al, Chromatographia 1977, 10(9) 545–8.

Helmich et al. (1980), "Isolation of 14–methyl hexadecanoic acid from wool fat . . . " J. Chromatography, 193(1) pp. 153–156.

Wertz et al., "Integral lipids of human hair" Lipids (1988), 23(9), pp. 878–881 (Abstracts Provided).

Patent Abstracts of Japan, vol. 10, No. 148 (C–350)(2205), May 29, 1986, & JP–A–61–7205; Jan. 13, 1986, K. Adachi, "Cell Activator".

*Primary Examiner*—Melvyn I. Marquis
*Assistant Examiner*—Robert H. Harrison
*Attorney, Agent, or Firm*—Oblon, Spivak, McClelland, Maier, & Neustadt

[57] ABSTRACT

A hair cosmetic composition comprising a branched fatty acids of the following formula (1),

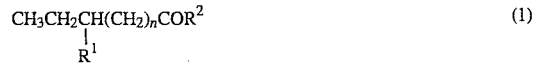

wherein $R^1$ is a methyl or ethyl group, n is an integer of 4–16, and $R^2$ is an amino, alkoxy, or glycerol group. The composition imparts excellent sensation to hair and prevents hairs from being damaged.

24 Claims, No Drawings

HAIR COSMETIC COMPOSITION

BACKGROUND OF THE INVENTION

1. Field of the Invention

The present invention relates to a hair cosmetic composition, and more particularly, to a hair cosmetic composition comprising a fatty acid with a branched chain. The hair cosmetic composition provides an excellent feeling to the hair and exhibits a superior effect of preventing damages to the hair.

2. Description of the Background Art

Recently, long hairs are in fashion among a number of people. A variety of long hair styles require sophisticated hair treatment techniques, including partial permanent wave treatments. These hair dressing treatments, however, very frequently involve damage to the hairs, producing splits or fractured hairs.

Such damage to hair is considered to be caused by the denaturing of keratinous proteins due to treatment of hair by chemicals, such as permanent wave treatments, making the hair fragile and more susceptible to damage by physical forces, e.g., drying, blushing, etc.

In order to prevent hair from being damaged by chemical treatments which may cause the denaturing of protein structures and, further, in order to promote formation of protective films on the hair surfaces or to improve its moisturizing property or flexibility, a variety of compounds such as collagens, keratinous proteins, and the like have been used in hair-care products. Various oil components such as higher alcohols, esters, liquid paraffins, and silicone oils are also incorporated in hair rinse compositions, hair treatment compositions, hair blushing compositions, and the like in order to decrease the friction forces between hair surfaces.

Although some effects can be expected of proteins, such as collagens and keratins, on the prevention of damage to hair due to chemical treatments, such effects are not necessarily sufficient. Oil components can exhibit some degree of effects on the prevention of damage to hair by lowering frictions between the hair surfaces and by temporarily providing an improved feeling during use. Such effects, however, do not last long on already damaged hair, giving only insufficient treatment effects. In addition, incorporation of a large amount of oil components results in sticky, oily feelings upon use.

Therefore, development of a hair cosmetic composition providing an excellent conditioning effects without sticky, oily feelings, but giving a moist sensation and acting on the damaged hairs so as to restore and keep the inherent functions of the hairs has been desired.

In view of this situation, the present inventors have undertaken extensive studies and have found that a hair cosmetic composition to which a fatty acid with a specific type of branched chain or its derivative is incorporated, when applied to hairs which had been chemically treated, e.g., perm treated hairs, surprisingly gave the hairs excellent moist, soft, smooth, and glossy conditioning effects which continued to persist after repeated shampooings.

SUMMARY OF THE INVENTION

Accordingly, an object of the present invention is to provide a hair cosmetic composition comprising a branched fatty acid of the following formula (1),

wherein $R^1$ is a methyl or ethyl group, n is an integer of 4–16, and $R^2$ is the following group (i), (ii), or (iii),

wherein $R^3$ is a cation selected from the group consisting of alkali metals, alkaline earth metals, ammonium ion, and organic ammonium ions; a hydrogen atom; or a $C_{1-6}$ alkyl or alkenyl group,

wherein $R^4$ and $R^5$ individually represents a hydrogen atom, or a $C_{1-6}$ alkyl or alkenyl group which may be substituted by a hydroxy group, or

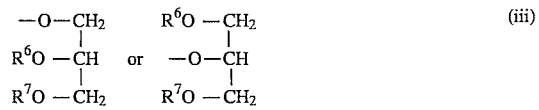

wherein $R^6$ and $R^7$ individually represents a hydrogen atom, an alkyl, alkenyl, or acyl group having 1–22 carbon atoms, or a group

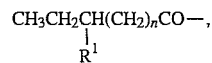

wherein $R^1$ and n have the same meanings as defined above.

Other objects, features and advantages of the invention will hereinafter become more readily apparent from the following description.

DETAILED DESCRIPTION OF THE INVENTION AND PREFERRED EMBODIMENTS

Included in the branched fatty acids represented by the above formula (1) (such a branched fatty acid is hereinafter referred to as component (A)) which are used in the cosmetic composition of the present invention are, besides the acids themselves, their esters, acid amides, and glycerides. In formula (1), although n represents an integer of 4–16, a preferable range is 8–16. Examples given for the alkyl or alkenyl groups substituted or unsubstituted by a hydroxy group and having 1–6 carbon atoms, which are represented by $R^3$, $R^4$, or $R^5$, are methyl, ethyl, n-propyl, i-propyl, n-butyl, t-butyl, amyl, n-hexyl, hydroxyethyl, hydroxypropyl, hydroxypentyl, hydroxyhexyl, vinyl, propenyl, butenyl, and the like. Given as examples of salts of these branched fatty acids are salts of alkali metals, e.g., sodium, lithium, potassium, etc.; salts of alkaline earth metals, e.g., calcium, magnesium, etc.; ammonium salts; organic ammonium salts, e.g., triethanolamine, diethanolamine, monoethanolamine, etc; salts of basic amino acid, e.g., lysine, arginine, etc.

The branched fatty acids (1) can be obtained by the separation and extraction from hair or the like according to the method described, for example, in Lipids, Vol. 23, No. 9, 878–881 (1988). Alternatively, they can be synthesized by the following process.

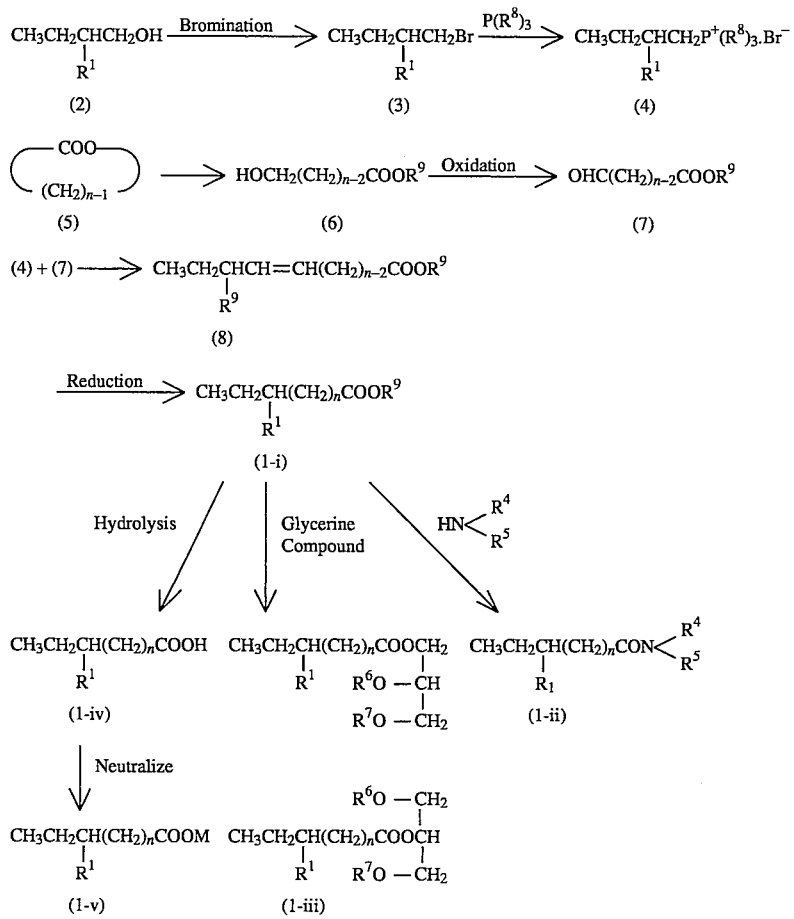

wherein $R^8$ is a saturated or unsaturated hydrocarbon group, $R^9$ is an alkyl or alkenyl group having 1–6 carbon atoms, M represents a cation selected from the group consisting of alkali metals, alkaline earth metals, ammonium ion, and organic ammonium ions; $R^1$, $R^3$, $R^4$, $R^5$, $R^6$, $R^7$, and n have the same meanings as defined above.

According to the above reaction scheme, a phosphonium salt (4) obtained from a 2-branched butanol (2) and an aldehyde compound (7) prepared from lactone (5) are subjected to the Wittig reaction to produce a branched unsaturated fatty acid (8). Branched fatty acid ester (1-i) can be obtained by reducing the branched unsaturated fatty acid (8). The reaction of the branched fatty acid ester (1-i) with an amine or a glycerine compound gives an amide compound (1-ii) or a glyceride (1-iii), respectively. The hydrolysis of the branched fatty acid ester (1-i) affords a free branched fatty acid (1-iv), which is neutralized to produce a salt of branched fatty acid (1-v). Each reaction step is illustrated in more detail by the following description.

A combination of hydrobromic acid-concentrated sulfuric acid or $CBr_4$-$PPh_3$, or $PBr_3$, can be used for the bromination of 2-branched butanol (2). 2-Methyl butanol, 2-ethyl butanol, and the like are given as examples of raw material 2-branched butanol (2). 2-Branched bromobutane (3) obtained by the reaction is subjected to a conventional post treatment and purified by distillation, before it is processed in the next step.

The reaction of the 2-branched bromobutane (3) and a phosphine compound can be carried out by heating these compounds in a non-polarized solvent with a comparatively high boiling point, e.g., benzene, xylene, etc., with refluxing for 1–100 hours. Triphenylphosphine, trimethylphosphine, and the like are given as examples of the phosphine compounds which can be used for the reaction.

The ring-opening reaction of a lactone compound (5) can be carried out by heating a mixture of the lactone compound and an alcohol in the presence of a basic catalyst. Given as examples of lactone compounds are γ-butyrolactone, δ-valerolactone, ε-caprolactone. 12-dodecanolide, 13-tridecanolide, 14-tetradecanolide, 15-pentadecanolide, 16-hexadecanolide, and the like.

The oxidation of ω-hydroxy fatty acid (6) is carried out in a solvent such as methylene chloride in the presence of an oxidation agent such as pyridinium chlorochromate or the like, usually, at room temperature, with stirring for 0.5–5 hours.

The reaction of compounds (4) and (7) can be carried out under the conventional Wittig reaction conditions, for example, by dissolving or dispersing the phosphonium salt (4) into a sufficiently dried ether solvent such as tetrahydrofuran, dioxane, diethyl ether, or the like in a nitrogen stream, adding to it 1–2 equivalent of alkyl lithium, aralkyl lithium, or aryl lithium, e.g., phenyl lithium, butyl lithium, or the like, and stirring for 10–60 minutes, usually, at room temperature, followed by the addition of equivalent mol of compound (7) which is dissolved in the same ether solvent in advance, under a nitrogen stream and stirring for 0.5–5 hours, usually, at room temperature.

The reduction of branched unsaturated fatty acid (8) can be carried out under a conventional catalytic reduction conditions, for example, by using a noble metal catalyst, e.g., palladium black, platinum black, Raney nickel, palladium on carbon, platinum on carbon, platinum oxide, etc., preferably platinum oxide, in a solvent, such as dioxane, acetic acid, ethanol, or the like, at room temperature to 100° C under hydrogen pressure of 1–100 atm. for 1–10 hours.

The conversion of branched fatty acid ester (1-i) into an amide compound can be carried out according to a conventional method, for example, by heating the branched fatty acid ester (1-i) and an amine compound at 50°–200° C. in the absence or the presence of an alkaline catalyst.

The reaction of the branched fatty acid ester (1-i) and a glycerine compound, e.g., glycerine, a fatty acid ester of glycerine, glycerine alkyl ether, etc., can be performed according to a conventional method, e.g., when the glycerine has a free hydroxy group, by the esterification reaction using an acid catalyst; and when the glycerine compound is a triglyceride, by the ester exchange reaction by using an alkaline catalyst.

The branched fatty acid (1-iv) can be obtained by converting the ester (1-i) into a salt by heating it in the presence of a basic catalyst, e.g., sodium hydroxide, followed by the neutralization of the salt with an acid. The branched fatty acid salt (1-v) can be obtained by neutralizing branched fatty acid (1-iv) with a hydroxide of alkali metal or alkaline earth metal, ammonia, or an amine, e.g., dimethylamine.

These branched fatty acids (1) thus obtained can be used either singly or in,combination of two or more.

The amount of branched fatty acids (1) to be incorporated into the hair cosmetic composition of the present invention is 0.01–20% by weight, and particularly preferably 0.2–10% by weight. The effects of the present invention can not be sufficiently exhibited with an amount smaller than 0.01% by weight, while an amount exceeding 20% by weight may result in a hair cosmetic composition with an impaired feeling, e.g., a sticky feeling. The hair cosmetic composition of the present invention includes all cosmetic compositions used for hair, e.g., pre-shampoo compositions, shampoo compositions, hair rinse compositions, hair conditioning compositions, hair treatment compositions, set lotion compositions, blow styling compositions, hair spray compositions, foam hair styling compositions, jelly-like hair styling compositions, hair liquid compositions, hair tonic compositions, hair cream compositions, permanent wave first liquid compositions,-permanent wave second liquid compositions, permanent hair dye compositions, temporary hair dye compositions, and the like. They may be any form depending on the manner by which they are applied, including aqueous solutions, ethanol solutions, emulsions, suspensions, gels, liquid crystals, aerosols, and the like.

Component (A) can be used in combination with one or more surface active agents of various kinds. Included in such surface active agents are anionic surface active agents such as alkylbenzene sulfonates, alkyl ether sulfates, olefin sulfonate, α-sulfo-fatty acid esters, amino acid type surface active agents, phosphate type surface active agents, sulfosuccinate type surface active agents, and the like; amphoteric surface active agents, such as sulfonic acid type, betaine type, alkylamine oxide type, and imidazoline type surface active agents; nonionic surface active agents such as polyoxyethylene alkyl ethers, polyoxyethylene alkyl phenyl ethers, alkanol amides and their alkylene oxide adducts, esters of polyhydric alcohol and fatty acid, sorbitan fatty acid ester, alkyl saccharide type surface active agents, and the like; and cationic surface active agents such as mono- or di-linear long chain alkyl quaternary ammonium salts, mono- or di-branched long chain alkyl quaternary ammonium salts, and the like. Among these, in view of low irritation to the skin and hair especially preferable surface active agents to be used in combination with component (A) are amino acid type, phosphate type, sulfo-succinate type, imidazoline type, and alkyl saccharide type surface active agents.

Among these combinations, the combination of cationic surface active agents (hereinafter referred to as component (B)) with component (A) produces hair cosmetic compositions which can provide hair with improved feeling to the touch.

Given as examples of cationic surface active agents which can be preferably used as component (B) are quaternary ammonium salts of formula (9) or (10).

(9)

(10)

wherein at least one of $R^{10}$, $R^{11}$, $R^{12}$, and $R^{13}$ is an alkyl or alkenyl group which may be substituted by an alkoxy, alkenyloxy, alkanoylamino, or alkenoylamino group and which contains 8–28 carbon atoms in total, with the other groups being benzyl $C_{1-5}$ alkyl, or $C_{1-5}$ hydroxyalkyl, $R^{14}$ is a $C_{2-3}$ alkylene group, $X^-$ is a halogen ion or an organic anion, and n is an integer of 1–20.

Among the above cationic surface active agents, quaternary ammonium salts of formula (9) are preferable, and among compounds of formula (9) especially preferable are quaternary ammonium salts of the following formulae (11)–(13).

(11)

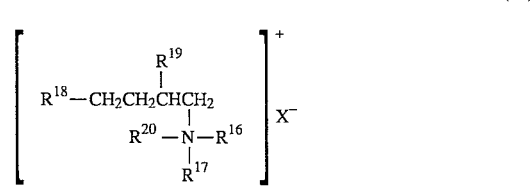

(12)

-continued

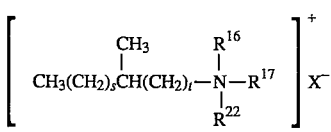
(13)

In the above formulae, $R^{15}$ is a mixture of (a) branched alkyl groups represented by the formula,

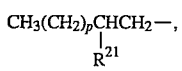

wherein $R^{21}$ is a methyl or ethyl group and p is an integer to make the total carbon atoms in the alkyl group 8–16, and (b) linear alkyl groups, $CH_3(CH_2)_q—$, wherein q is an integer of 7–15, and wherein the branched ratio, (a)/(a)+(b) is in the range of 10–100%. $R^{16}$ and $R^{17}$ are individually a benzyl group or a $C_{1-3}$ alkyl or hydroxy alkyl group, and $R^{18}$ and $R^{19}$ are individually a $C_{2-12}$ alkyl group, $R^{20}$ is a group,

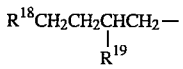

or a $C_{1-3}$ alkyl group, $R^{22}$ is a $C_{1-3}$ alkyl group, or a group,

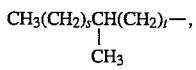

wherein s is an integer of 2–14 and t is an integer of 3–11, with a proviso that the sum s+t is 9–21 and $X^-$ is a halogen ion or an organic anion.

The branched quaternary ammonium salts represented by formula (11) can be prepared, for example, from $C_{8-16}$ oxo alcohols by synthesis. Specific examples given of such compounds are dialkyldimethyl ammonium salt, dialkylmethylhydroxyethyl ammonium salt, dialkylmethylbenzyl ammonium salt, and the like, having alkyl groups derived from oxo alcohols.

Among the range of the branched ratio, 10–100%, of $R^{15}$ in compounds of formula 11), particularly preferable ratio is 10–50%. With respect to the total carbon atom numbers for $R^{15}$, which are usually 8–16, a mixture having a specified carbon atom distribution is preferably used. An example of particularly preferable carbon atom distribution is as follows.

$C_{8-11}$: less than 5%
$C_{12}$: 10–35%
$C_{13}$: 15–40%
$C_{14}$: 20–45%
$C_{15}$: 5–30%
$C_{16}$: less than 5%

Specific examples of such branched quaternary ammonium salts are dialkyldimethyl ammonium chlorides having alkyl groups with 8–16 carbon atoms and the branched ratio of 10–50%.

The branched quaternary ammonium salts represented by formula (12) are usually synthesized from $C_{8-28}$ Guerbet alcohol of the formula shown below. Preferable examples of such branched quaternary ammonium salts are alkyltrimethyl ammonium salt, alkyldimethylbenzyl ammonium salt:, dialkyldimethyl ammonium salt, dialkylmethylhydroxyethyl ammonium salt, dialkylmethylbenzyl ammonium salt:, and the like, having alkyl groups derived from Guerbet alcohols. Especially preferable compounds among these are 2-decyltetradecyltrimethyl ammonium chloride, 2-dodecylhexadecyltrimethyl ammonium chloride, di-2-hexyldecyldimethyl ammonium chloride, di-2-octyldodecyldimethyl ammonium chloride, and the like.

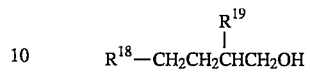

Preferable branched quaternary ammonium salts represented by formula (13) are those having the sum of s and t of 15.

Specific examples given of $X^-$ which is the counter ion of the branched quaternary ammonium salts represented by formulae (9), (10), (11), (12), and (13) are halogen ions such as chlorine, bromine, iodine; and organic anions such as methosulfate, ethosulfate, methophosphate, ethophosphate, and the like.

It is desirable that these surface active agent be incorporated into the hair cosmetic composition of the present invention in an amount of 0.01–40.0% by weight, and particularly preferably 0.05–20.0% by weight.

In order to further improve the feeling to the touch of the skin and hair, one or more cationic polymers (hereinafter referred to as component (C)) can be incorporated into the hair cosmetic composition of the present invention. Such cationic polymers may include cationized cellulose derivatives, cationic starch, cationized guarh-gum derivatives, copolymers of diallyl quaternary ammonium salt and acrylamide, quaternarized polyvinylpyrrolidone derivatives, polyglycol-polyamine condensates, and the like.

Preferable cationic polymers among these compounds are cationized cellulose derivatives with a molecular weight of about 100,000–3,000,000, cationic starch with a cationized degree of about 0.01–1, cationized guarh-gum derivatives with a cationized degree of about 0.01–1 (e.g., Jaguar manufactured by Meyhall Chemical AG.), copolymers of diallyl quaternary ammonium salt and acrylamide with a molecular weight of about 30,000–2,000,000, quaternarized polyvinylpyrrolidone derivatives with a molecular weight of about 10,000–2,000,000 and in which vinyl polymers contain 1.8–2.4% of cationic nitrogen atoms (e.g., quaternarized polyvinylpyrrolidone-dimethylaminoethyl methacrylate copolymer), polyglycol-polyamine condensates having a $C_{6-20}$ alkyl group, copolymers of adipic acid and dimethylaminohydroxypropyldiethylenetriamine (CARTARETINE, a product of Sandoz Inc.), as well as cationic polymers described in Japanese Patent Laid-open (ko-kai) Nos. 139734/1978 and 36407/1985, and the like.

It is desirable that these cationic polymers (component (c)) be incorporated into the hair cosmetic composition of the present invention in an amount of 0.05–20.0% by weight, and particularly preferably 0.1–10.0% by weight.

In order to further improve the feeling to the touch of the skin and hair, one or more silicone derivatives (hereinafter referred to as component (D)) can be incorporated into the hair cosmetic composition of the present invention.

Given as examples of silicone derivatives which can be used in the present invention as component (D) are compounds described in (1)–(9) below.

(1) Dimethylpolysiloxane of the following formula.

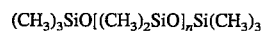

wherein n=3–20,000.

(2) Methylphenylpolysiloxane of the following formula (14) and (15)

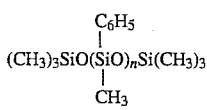
(14)

wherein n=1–20,000.

$(CH_3)_3SiO[(CH_3)_2SiO]_\alpha[(C_6H_5)_2SiO]_\beta Si(CH_3)_3$ (15)

wherein $\alpha+\beta$=1–500.

(3) Polyether-modified silicone of the following formulae (16)–(19).

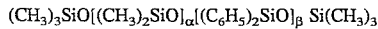
(16)

wherein A' is a $C_{1-12}$ alkyl group or a hydrogen atom, x1 is a number of 1–100, preferably 3–30, y1 is a number of 1–50, preferably 3–30, m1 is a number of 1–50, preferably 3–30, and n1 is a number of 0–50, preferably 0–30, provided that the sum of x1 and y1 is greater than 15 and the sum of m1 and n1 is greater than 5.

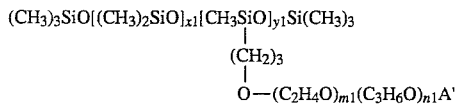
(17)

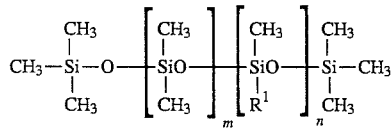
(18)

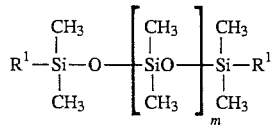
(19)

wherein $R_1$ is —$(CH_2)_3$—O—$(C_2H_4O)_x(C_3H_6O)_y$—A, wherein A is a $C_{1-12}$ alkyl group or a hydrogen atom, X is 0–50 and y is 0–50, provided that x+y≧1, m is a number of 1–2,000 and n is a number of 1–1,000.

(4) Epoxy-modified silicone of the following formula.

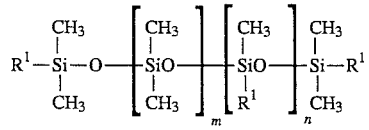

wherein x2 is a number of 1–500, preferably 1–250, y2 is a number of 1–50, preferably 1–30, and $R^{20}$ is a $C_{1-3}$ alkylene group.

(5) Fluorine-modified silicone of the following formula.

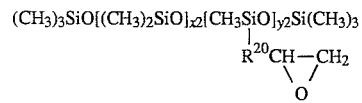

wherein x3 is a number of 1–400, preferably 1–250.

(6) Alcohol-modified silicone of the following formulae (20) and (21).

$HO(CH_2)$—$R^{21}$—$[(CH_3)_2SiO]_{x4}(CH_3)2SiR^{21}$—$CH_2OH$ (20)

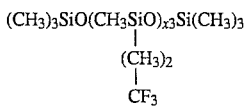
(21)

wherein x4 and y4 is individually a number of 1–500, preferably 1–200, and $R^{21}$ is a $C_{m'}H_{2m'}$, wherein m' is 0–4.

(7) Alkyl-modified silicone of the following formulae (22) and (23).

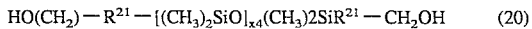
(22)

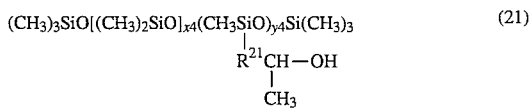
(23)

wherein x5 and y5 is individually a number of 1–500, preferably 1–200, $R^{22}$ is a $C_{2-18}$ alkyl group, $R^{23}$ is a $C_{m'}H_{2m'}$, wherein m' is 0–4, and $R^{24}$ is a $C_{10-16}$ alkyl group.

(8) Alkoxy-modified silicone of the following formula (24).

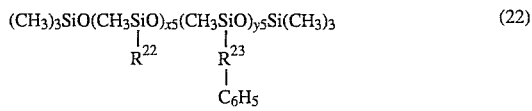
(24)

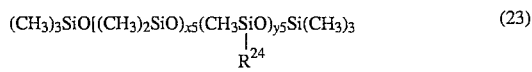

wherein $R^{26}$ is a methyl or phenyl group, l is an integer of 1–3,000, m and n are numbers satisfying an equation m+n= 1–500, $R^{22}$ is a $C_{1-28}$ alkyl group, preferably a $C_{12-22}$ alkyl group, and k is an integer of 0–6.

(9) Amino-modified silicone of the following formulae (25) and (26).

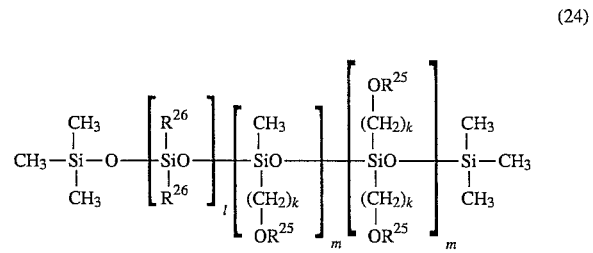
(25)

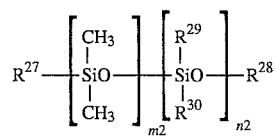

-continued

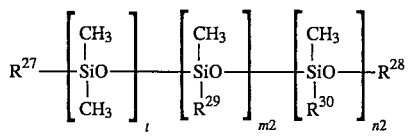
(26)

wherein $R^{27}$ are a methyl or hydroxy group, $R^{28}$ is a methyl group or a hydrogen atom, $R^{29}$ is a group represented by the following formula (i) or (ii), $R^{30}$ is a hydroxy, hydroxy alkyl, oxyalkylene, or polyoxyalkylene group, and l, m2, and n2 is integers depending on the molecular weight.

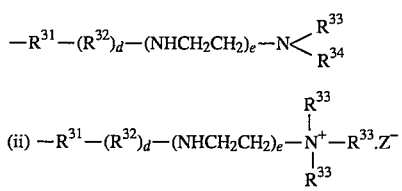

wherein $R^{31}$ is a divalent hydrocarbon group, $R^{32}$ is a group

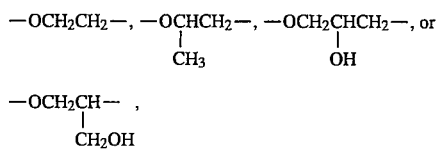

$R^{33}$ and $R^{34}$ are individually a hydrogen atom or a monovalent hydrocarbon group, d and e are integers of 0–6, an Z is a halogen or an organic anion.

Among the above compounds especially preferable amino-modified silicone compounds are those represented by the following formula.

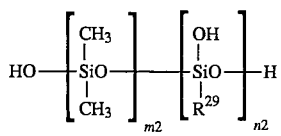

wherein $R^{29}$, m2 and n2 have the same meanings as defined above.

Of the above amino-modified silicone compounds, those represented by the following formula having an average molecular weight of 3,000–100,000 are typical amino-modified silicone compounds described in the name of AMODIMETHICONE in CTFA Dictionary, third edition (Cosmetic Ingredient Dictionary, USA).

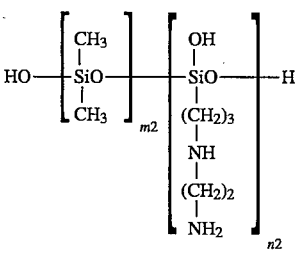

wherein m2 and m2 are the same as defined above.

It is desirable that the above amino-modified silicone compounds be used in the form of an aqueous suspension. Such an aqueous suspension can be obtained, for example, according to the method described in Japanese Patent Publication (kokoku) No. 38609/1981, by the emulsion polymerization of a cyclic diorganopolysiloxane and an organodialkoxysilane having an aminoalkyl group and a hydroxy, hydroxy alkyl, oxyalkylene, or polyoxyalkylene group, in the presence of a quaternary ammonium salt surfactant and water. When the above amino-modified silicone compounds are used in the form of an aqueous suspension, their concentration in the suspension is usually 20–60% by weight, and preferably 30–50% by weight.

Preferred commercially available amino-modified silicone compounds in the form of an aqueous suspension are SM 8702C (a product of Toray Silicone Co.), DC 929 (a product of Dow Corning Co.), and the like.

Of the above silicone derivatives, dimethylpolysiloxane with a polymerization degree of greater than 500, polyether-modified silicone compounds, amino-modified silicone compounds, and cyclic silicone compounds are particularly preferable, because they can give an exceptionally fine sensation to the hair.

Silicone derivatives, as Component (D), are incorporated in the hair cosmetic composition of the present invention in an amount 0.01–20.0% by weight, and preferably 0.05–10.0% by weight.

Furthermore, in order to promote the characteristics of the hair cosmetic composition of the present invention of providing flexibility and moisture feelings to the hair, one or more monoalkyl ethers of mono- or polyalkylene glycol can be added as Component (E).

Ethylene glycol monoalkyl ether, propylene glycol monoalkyl ether, diethylene glycol monoalkyl ether, dipropylene glycol monoalkyl ether, and dialkylene glycol monoalkyl ether compounds represented by the following formula (27) are included in monoalkyl ethers of mono- or polyalkylene glycol used in the present invention as component (E). Among these, compounds of formula (27) are preferable. The following compounds are given as specific examples of component (E). Diethylene glycol monomethyl ether, diethylene glycol monoethyl ether, diethylene glycol monopropyl ether, diethylene glycol monobutyl ether, diethylene glycol monopentyl ether, diethylene glycol monoisopropyl ether, diethylene glycol mono-t-butyl ether, dipropylene glycol monomethyl ether, dipropylene glycol monoethyl ether, dipropylene glycol monopropyl ether, dipropylene glycol monobutyl ether, dipropylene glycol monoisopropyl ether, dipropylene glycol mono-t-butyl ether, and the like. Of these, especially preferable are diethylene glycol monoethyl ether, diethylene glycol monopropyl ether, and diethylene glycol monobutyl ether.

wherein $R^{30}$ is a hydrogen or a methyl group, $R^{31}$ is a $C_{1-5}$ alkyl group.

A preferable amount of component (E) to be incorporated in the hair cosmetic composition of the present invention is 1.0–50.0% by weight with especially preferable range being 5.0–30.0% by weight.

Particularly good results are obtained by the following combinations of components (A)–(E).

(1) (A)+(B)
(2) (A)+(C)
(3) (A)+(D)
(4) (A)+(E)
(5) (A)+(B)+(C)
(6) (A)+(B)+(D)
(7) (A)+(B)+(E)

In the above combinations, a preferable ratio by weight of component (A) and one of other components (C), (D), and (E) in the hair cosmetic composition is in the range of 10/1 to 1/10.

In addition to the above components, other various components may be optionally added to the hair cosmetic composition of the present invention to the extent that the effects of the present invention are not adversely affected. Such optional components include sensation improvers such as salts of higher fatty acid, alkylamine oxides, fatty acid alkanolamides, squalane, lanoline, α-monoisostearyl glyceryl ether, cholesteryl sulfates, and the like; humectants such as propylene glycol, glycerine, sorbitol, and amide derivatives represented by the following formula,

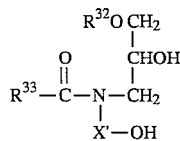

wherein $R^{32}$ is a linear or branched, saturated or unsaturated hydrocarbon group having 10–26 carbon atoms, $R^{33}$ is a linear or branched, saturated or unsaturated hydrocarbon group having 9–25 carbon atoms, and X' represents a group —$(CH_2)_m$—, wherein m is an integer of 2–6 (disclosed in Japanese Patent Laid-open (kokai) No. 9913/1989); viscosity adjusting agents such as methyl cellulose, carboxyvinyl polymers, hydroxyethyl cellulose, polyoxyethylene glycol distearate, ethanol, and the like; pearlescent agents; perfumes; pigments; UV absorbers; antioxidants; bactericidal agents such as trichlosan, trichlorocarban, and the like; antiphlogistic agents such as potassium glycyrrhizicate, tocopherol acetate, and the like; antidandruffs such as zincpyrithion, octopirox, and the like; antiseptics such as methyl paraben, butyl paraben, and the like.

It is desirable that the hair cosmetic composition of the present invention be adjusted to pH 3–10, especially preferably pH 4–8, with an acidic or alkaline chemicals which is commonly used in cosmetic compositions.

The hair cosmetic composition of the present invention imparts an excellent sensation without sticky or oily feelings. It exhibits a superior effects on the prevention of damage to hairs, such as production of split or fractured hairs.

Other features of the invention will become apparent in the course of the following description of the exemplary embodiments which are given for illustration of the invention and are not intended to be limiting thereof.

EXAMPLES

Synthetic Example 1

Synthesis of 18-Methyleicosanoic Acid (1) Synthesis of 2-methylbromobutane 52 gm of concentrated sulfuric acid and 161 gm of 48% hydrobromic acid were added to 65 gm of 2-methylbutanol, and the mixture was gently refluxed for 72 hours. The resultant reaction solution was subjected to steam distillation to produce a distilled fraction containing 2-methylbromobutane. The water layer of the distilled fraction was discharged and the oil layer was washed, with 7.8 gm of cold concentrated sulfuric acid, 10 gm of 10% aqueous solution of sodium carbonate, and 10 gm of water. The product was dried over calcium chloride overnight, followed by distillation to obtain 80.8 gm of 2-methylbromobutane (yield: 72%).

$^1$H-NMR (200 MHz, CDCl$_3$) δ: 0.91(3H, t, J=7.4Hz), 1.01(2H, t, J=6.6Hz), 1.17– 1.88(3H, m), 3.37ppm(2H, m).

(2) Synthesis of 2-methylbutyltriphenylphosphonium bromide 30.9 gm of 2-methylbromobutane and 53.7 gm of triphenylphosphine were dissolved into 50 ml of benzene and the mixture was refluxed for 88 hours. Crystals deposited were collected by filtration, washed with benzene, and dried to produce 15.7 gm of 2-methylbutyltriphenylphosphonium bromide (yield: 42%). The product was submitted to the next step without purification.

(3) Synthesis of methyl 16-hydroxyhexadecanoate 76.3 gm of 16-hexadecanolide and 0.29 gm of 28% sodium methoxide solution were dissolved into 250 gm of methanol, and the solution was heated at 60° C. for 60 hours while stirring. The reaction mixture was cooled to deposit crystals. The crystals were collected by filtration, washed, and dried to obtain 77.5 gm of methyl 16-hydroxyhexadecanoate (yield: 90.2%).

mp: 54.2° C.

IR (KBr) Nu 3370 cm$^{-1}$ (OH), 1744 cm$^{-1}$ (C=O)

$^1$H-NMR (200 MHz, CDCl$_3$) δ: 1.26(22H, bs.), 1.64(4H, m), 2.30(2H, t, J=7.5Hz), 3.64(2H, t, J=6.6Hz), 3.66ppm(3H, s).

(4) Synthesis of methyl 15-formylpentadecanoate 65.6 gm of pyridinium chlorochromate was dissolved into 400 ml of methylene chloride. To the solution was added 55 gm of methyl 16-hydroxyhexadecanoate which had been dissolved in 40 ml of methylene chloride in advance. After stirring for 2 hours at room temperature, 400 ml of anhydrous diethyl ether was added. The supernatant was removed and the insolbles were washed three times with 100 ml of anhydrous diethyl ether. The supernatant and the washing were combined together and passed through 40 gm of a silica gel column, and the eluent was concentrated under reduced pressure. The crude crystals thus obtained were purified by flash column chromatography (chloroform:hexane=4:1) to obtain 43.6 gm of methyl 15-formylpentadecanoate.

mp: 41.5° C.

IR (KBr) Nu 3370 cm$^{-1}$ (OH), 1737 cm$^{-1}$ (C=O)

$^1$H-NMR (200 MHz, CDCl$_3$) δ: 1.26(20H, bs.), 1.62(2H, m), 2.30(2H, t, J=7.5Hz), 3.66(3H, s), 9.76 ppm(1H, d, J=2.0Hz).

(5) Synthesis of methyl 18-methyl-16-eicosenoate 13 gm of 2-methylbutyltriphenylphosphonium bromide was pulverized and dispersed into 130 ml of anhydrous tetrahydrofuran. To this was added 23.7 ml of 1.5M butyl lithium-hexane solution under a nitrogen atmosphere and the mixture was stirred for 30 minutes. To the solution was slowly added 8.4 gm of methyl 15-formylpentadecanoate which had been dissolved in 130 ml of anhydrous tetrahydrofuran in advance. After stirring for 3 hours, the solvent was evaporated. The crude crystals thus obtained were purified by flash column chromatography (chloroform:hexane=1:1) to obtain 5.3 gm of methyl 18-methyl-16-eicosenoate (yield: 51%). The product was submitted to the next step without purification.

(6) Synthesis of 18-methyleicosanoic acid 5.3 gm of methyl 18-methyl-16-eicosenoate charged into an autoclave together with 0.3 gm of platinum oxide and 30 ml of acetic acid were reduced under 100 atm hydrogen pressure at 100° C. for 5 hours. After the reaction, the catalyst was removed by filtration and the solvent was evaporated to obtain 3 gm of methyl 18-methyleicosanoate, which was purified by flash column chromatography (chloroform). The product was dissolved into 150 ml of a 5% sodium hydroxide-ethanol solution and stirred at room temperature for 8 hours. Then, 95 ml of 2N sulfuric acid was added to obtain a solid. The solid material was filtered and washed with water to obtain 3.1 gm of 18-methyleicosanoic acid (yield: 59% from methyl 18-methyl-16-eicosenoate).

mp: 53° C.

MS 340 (M$^+$) (As methyl ester).

IR (KBr) Nu 1704 cm$^{-1}$ (C=O).

$^1$H-NMR (200 MHz, CDCl$_3$) δ: 0.85(6H, t, J=6.25Hz), 1.26(31H, bs.), 1.63(2H,m), 2.34(2H, t, J=7.2Hz), 10.1 ppm(1H, bs).

$^{13}$C-NMR (200 MHz, CDCl$_3$) δ: 11.43, 19.24, 24.73, 27.18, 29.13, 29.31, 29.55, 29.67, 29.79, 30.11, 34.19, 34.45, 36.70, 180. 7ppm.

Example 1

Shampoo compositions shown in Table 1 were prepared and their performances were evaluated.

Methods of Evaluation (1) Hair tresses (20 gm, about 15–20 cm long) of Japanese women, which had been cold permed at least three times, were wetted with warm water of about 40° C., and well lathered with about 1 gm of the shampoo composition for 1 minutes, following which the hair was washed with a stream of water and dried. The dried hair was evaluated in terms of its flexibility, oily sensation, moistened sensation, and smoothness, and rated according to the following standard.

Flexibility:
 AAA: Very flexible
 BBB: Soft
 CCC: Cannot tell whether soft or hard
 DDD: Hard Oily Sensation:
 AAA: Hardly felt oily
 BBB: Oily sensation is very slight
 CCC: Cannot tell whether the sensation is oily or not
 DDD: Imparts an oily sensation Gloss:
 AAA: Very glossy
 BBB: Glossy
 CCC: Cannot tell whether the hair is glossy or not
 DDD: Not glossy Smoothness:
 AAA: Very smooth
 BBB: Smooth
 CCC: Cannot tell whether the sensation is smooth or not
 DDD: Not smooth (2) Hair tresses shampooed in the same way in (1) above were blushed a prescribed times to evaluate the degree of split hair production before and after the blushing.

AAA: No increase in split hairs was recognized
BBB: Increase in split hairs was hardly recognized
CCC: Increase in split hairs was slightly recognized
DDD: Increase in split hairs was remarkable

TABLE 1

|  | Invention Composition | | | | | Comparative Composition | |
| --- | --- | --- | --- | --- | --- | --- | --- |
|  | 1 | 2 | 3 | 4 | 5 | 1 | 2 |
| Sodium polyoxyethylene (2.5) lauryl sulfate | 20 | — | — | — | — | 20 | — |
| Triethanolamine polyoxyethylene (2.5) lauryl sulfate | — | 20 | — | — | — | — | 20 |
| Triethanolamine lauryl sulfate | — | — | 20 | — | — | — | — |
| TEA salt of N-lauroyl-N'-carboxymethyl-N'-(2-hydroxyethyl) ethylenediamine | — | — | — | 20 | — | — | — |
| Disodium polyethylene (3) laurylsulfosuccinate | — | — | — | — | 20 | — | — |
| Triethanolamine 18-methyleicosanoate | 5 | 5 | 5 | — | — | — | — |
| Methyl 18-methyleicosoanoate | — | — | — | 5 | 5 | — | — |
| Water | Balance | | | | | | |
| Evaluation Items | | | | | | | |

TABLE 1-continued

|  | Invention Composition | | | | | Comparative Composition | |
| --- | --- | --- | --- | --- | --- | --- | --- |
|  | 1 | 2 | 3 | 4 | 5 | 1 | 2 |
| Flexibility | AAA | AAA | AAA | AAA | AAA | DDD | DDD |
| Oily Sensation | BBB | BBB | BBB | BBB | BBB | DDD | DDD |
| Gloss | AAA | AAA | AAA | AAA | AAA | DDD | DDD |
| Smoothness | AAA | AAA | AAA | AAA | AAA | DDD | DDD |
| Split Hair Production | AAA | AAA | AAA | AAA | AAA | DDD | DDD |

Example 2

Hair treatment compositions shown in Table 2 were prepared and their performances were evaluated.

Methods of Evaluation (1) Hair tresses (20 gm, about 15–20 cm long) of Japanese women, which had been cold permed at least three times, were shampooed with a conventional normal shampoo. After washing, 2 gm of the hair treatment composition was evenly applied. The hair was rinsed with a stream of water, dried with towel, and evaluated while wetted. After drying with a drier, the hair was again evaluated according to the same methods as in Example 1. The results are shown in Table 2.

TABLE 2

|  | Invention Composition | | | Comparative Composition | |
| --- | --- | --- | --- | --- | --- |
|  | 6 | 7 | 8 | 3 | 4 |
| Stearyl trimethylammonium chloride | 2 | 2 | 2 | 2 | 2 |
| N-(2-decyl)tetradecyl-N,N,N-trimethyl-ammonium chloride | 2 | 2 | 2 | 2 | 2 |
| Cetyl alcohol | 5 | 5 | 5 | 5 | 5 |
| Potassium 18-methyleicosanoate | 1 | — | — | — | — |
| Methyl 18-methyleisocante | — | 1 | — | — | — |
| 18-Methyleicosanoate ethylamide | — | — | 1 | — | — |
| Water | Balance | | | | |
| Evaluation Items |  |  |  |  |  |
| Flexibility | AAA | AAA | AAA | BBB | BBB |
| Oily Sensation | AAA | AAA | AAA | BBB | BBB |
| Gloss | AAA | AAA | AAA | CCC | CCC |
| Smoothness | AAA | AAA | AAA | CCC | CCC |
| Split Hair Production | AAA | AAA | AAA | CCC | CCC |

Example 3

Shampoo compositions in which the following compounds (a)–(e) were incorporated instead of triethanolamine 18-methyleicosanoate of Example 1 were prepared.
 (a) Potassium 18-methyleicosanoate
 (b) Potassium 16-methyloctadecanoate
 (c) 2,3-Dihydropropyl 18-methyleicosanoate
 (d) 18-Methyleicosanoate ethylamide They exhibited superior flexibility, gloss, and smoothness.

Example 4

A conditioning mousse was prepared according to the following formulation.

| N-(2-decyl)tetradecyl-N,N,N-trimethylammonium chloride | 0.5 |
| --- | --- |
| Octyldodecyl stearate | 1.0 |
| Dipropylene glycol | 1.0 |
| SM8702C (a silicone derivative; a product of Toray-Dow Corning, Co.) | 0.3 |
| Glycerine | 2.5 |
| 18-Methyleicosanoic acid | 0.5 |
| Liquid paraffin | 2.5 |
| Polyoxyethylene sorbitan monostearate | 0.2 |
| Ethanol | 5.0 |
| Methyl paraben | 0.1 |
| Perfume | 0.1 |
| Propellant (LPG) | 10.0 |
| Water | Balance |
| Total | 100.0 |

Example 5

A shampoo composition was prepared according to the following formulation.

| TEA salt of N-lauroyl-N'-carboxymethyl-N'-(2-hydroxyethyl) ethylenediamine | 1.0 |
| --- | --- |
| 18-Methyleicosaoinic acid | 0.5 |
| Diethylene glycol monopropyl ether | 5.0 |
| Disodium polyoxyethylene (5) lauryl sulfocuccinate | 5.0 |
| Lauric acid diethanol amide | 2.0 |
| Coconut oil fatty acid amide propyl betain | 2.0 |
| Distearyldimethylammonium chloride | 0.1 |
| Cationized cellulose (Polymer JR400, a product of UCC) | 0.15 |
| Perfume | 0.5 |
| Pigment | 0.5 |
| Water | Balance |
| Total | 100.0 |

Obviously, numerous modifications and variations of the present invention are possible in light of the above teachings. It is therefore to be understood that within the scope of the appended claims, the invention may be practiced otherwise than as specifically described herein.

What is claimed is:

1. A hair cosmetic composition comprising 0.2 to 10% by weight of a compound of the following formula (1), $$CH_3CH_2CH(CH_2)_nCOR^2 \quad (1)$$
$$|$$
$$R^1$$

wherein $R^1$ is a methyl or ethyl group, n is an integer of 4–16, and $R^2$ is the following group (i), (ii), or (iii), $$-OR^3 \quad (i)$$

wherein $R^3$ is a cation selected from the group consisting of alkali metals, alkaline earth metals, ammonium ion, and organic ammonium ions; a hydrogen atom; or an alkyl or alkenyl group having 1–6 carbon atoms, $$-N{\overset{R^4}{\underset{R^5}{<}}} \quad (ii)$$

wherein $R^4$ and $R^5$ individually represents a hydrogen atom, or a $C_{1-6}$ alkyl or alkenyl group which may be substituted or unsubstituted by a hydroxy group, or $$\begin{array}{cc} -O-CH_2 & R^6O-CH_2 \\ | & | \\ R^6O-CH & \text{or} \quad -O-CH \\ | & | \\ R^7O-CH_2 & R^7O-CH_2 \end{array} \quad (iii)$$

wherein $R^6$ and $R^7$ individually represents a hydrogen atom, an alkyl, alkenyl, or acyl group having 1–22 carbon atoms, or a group $$CH_3CH_2CH(CH_2)_nCO-,$$
$$|$$
$$R^1$$

wherein $R^1$ and n have the same meanings as defined above, in admixture with a component selected from the group consisting of fatty acid alkanolamides, squalane, lanolin, α-monoisostearyl glyceryl ether, propylene glycol, glycerine, sorbitol, amide compounds represented by the following formula, $$\begin{array}{c} R^{32}OCH_2 \\ | \\ O \quad CHOH \\ \| \quad | \\ R^{33}-C-N-CH_2 \\ | \\ X'-OH \end{array}$$

(wherein $R^{32}$ is a linear or branched, saturated or unsaturated hydrocarbon group having 10–26 carbon atoms, $R^{33}$ is a linear or branched, saturated or unsaturated hydrocarbon group having 9–25 carbon atoms, and X' represents a group $-(CH_2)_m-$, wherein m is an integer of 2–6), methyl cellulose, carboxyvinyl polymers, hydroxyethyl cellulose, polyoxyethylene glycol distearate, ethanol, pearlescent agents, perfumes, pigments, UV absorbers, antioxidants, trichlosan, trichlorocarban, potassium glycyrrhizicate, tocopherol acetate, zincpyrithion, octopirox, methyl paraben, and butyl paraben.

2. The composition of claim 1, wherein said compound of formula (I) is selected from the group consisting of 18-methyleicosanoic acid, triethanolamine 18-methyleicosanoate, potassium 18-methyleicosanoate, methyl 18-methyleicosanoate, 18-methyleicosanoate ethylamide, potassium 16-methyloctadecanoate, and 2,3-dihydroxypropyl 18-methyleicosanoate.

3. The composition of claim 1, wherein said compound of formula (1) is triethanolamine 18-methyleicosanoate.

4. A hair cosmetic composition comprising the following components (A) and (B), (A) 0.2 to 10% by weight of one or more compounds of the following formula (1), $$CH_3CH_2CH(CH_2)_nCOR^2 \quad (1)$$
$$|$$
$$R^1$$

wherein $R^1$ is a methyl or ethyl group, n is an integer of 4–16, and $R^2$ is the following group (i), (ii), or (iii), $$-OR^3 \quad (i)$$

wherein $R^3$ is a cation selected from the group consisting of alkali metals, alkaline earth metals, ammonium ion, and organic ammonium ions; a hydrogen atom; or an alkyl or alkenyl group having 1–6 carbon atoms, $$-N{\overset{R^4}{\underset{R^5}{<}}} \quad (ii)$$

wherein $R^4$ and $R^5$ individually represents a hydrogen atom, or a $C_{1-6}$ alkyl or alkenyl group which may be substituted or unsubstituted by a hydroxy group, or $$\begin{array}{cc} -O-CH_2 & R^6O-CH_2 \\ | & | \\ R^6O-CH & \text{or} \quad -O-CH \\ | & | \\ R^7O-CH_2 & R^7O-CH_2 \end{array} \quad (iii)$$

wherein $R^6$ and $R^7$ individually represents a hydrogen atom, an alkyl, alkenyl, or acyl group having 1–22 carbon atoms, or a group $$CH_3CH_2CH(CH_2)_nCO-,$$
$$|$$
$$R^1$$

wherein $R^1$ and n have the same meanings as defined above, and (B) 0.01 to 40% by weight of one or more cationic surface active agents.

5. The composition of claim 4, wherein component (A) is selected from the group consisting of 18-methyleicosanoic acid, triethanolamine 18-methyleicosanoate, potassium 18-methyleicosanoate, methyl 18-methyleicosanoate, 18-methyleicosanoate ethylamide, potassium 16-methyloctadecanoate, and 2,3-dihydroxypropyl 18-methyleicosanoate.

6. The composition of claim 4, wherein component (A) is triethanolamine 18-methyleicosanoate.

7. A hair cosmetic composition comprising the following components (A) and (C), (A) 0.2 to 10% by weight of one or more compounds of the following formula (1),

wherein $R^1$ is a methyl or ethyl group, n is an integer of 4–16, and $R^2$ is the following group (i), (ii), or (iii), —$OR^3$      (i)

wherein $R^3$ is a cation selected from the group consisting of alkali metals, alkaline earth metals, ammonium ion, and organic ammonium ions; a hydrogen atom; or an alkyl or alkenyl group having 1–6 carbon atoms

wherein $R^4$ and $R^5$ individually represents a hydrogen atom, or a $C_{1-6}$ alkyl or alkenyl group which may be substituted or unsubstituted by a hydroxy group, or

wherein $R^6$ and $R^7$ individually represents a hydrogen atom, an alkyl, alkenyl, or acyl group having 1–22 carbon atoms, or a group

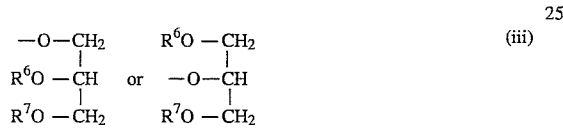

wherein $R^1$ and n have the same meanings as defined above, and (C) 0.05 to 20.0% by weight of one or more cationic polymers.

8. The composition of claim 7, wherein component (A) is selected from the group consisting of 18-methyleicosanoic acid, triethanolamine 18-methyleicosanoate, potassium 18-methyleicosanoate, methyl 18-methyleicosanoate, 18-methyleicosanoate ethylamide, potassium 16-methyloctadecanoate, and 2,3-dihydroxypropyl 18-methyleicosanoate.

9. The composition of claim 7, wherein component (A) is triethanolamine 18-methyleicosanoate.

10. A hair cosmetic composition comprising the following components (A) and (D), (A) 0.2 to 10% by weight of one or more compounds of the following formula (1),

wherein $R^1$ is a methyl or ethyl group, n is an integer of 4–16, and $R^2$ is the following group (i), (ii), or (iii), —$OR^3$      (i)

wherein $R^3$ is a cation selected from the group consisting of alkali metals, alkaline earth metals, ammonium ion, and organic ammonium ions; a hydrogen atom; or an alkyl or alkenyl group having 1–6 carbon atoms,

wherein $R^4$ and $R^5$ individually represents a hydrogen atom, or a $C_{1-6}$ alkyl or alkenyl group which may be substituted or unsubstituted by a hydroxy group, or

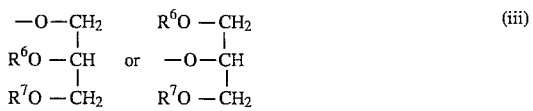

wherein $R^6$ and $R^7$ individually represents a hydrogen atom, an alkyl, alkenyl, or acyl group having 1–22 carbon atoms, or a group

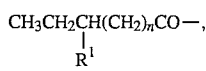

wherein $R^1$ and n have the same meanings as defined above, and (D) 0.01 to 20.0% by weight of one or more silicone compounds.

11. The composition of claim 10, wherein component (A) is selected from the group consisting of 18-methyleicosanoic acid, triethanolamine 18-methyleicosanoate, potassium 18-methyleicosanoate, methyl 18-methyleicosanoate, 18-methyleicosanoate ethylamide, potassium 16-methyloctadecanoate, and 2,3-dihydroxypropyl 18-methyleicosanoate.

12. The composition of claim 10, wherein component (A) is triethanolamine 18-methyleicosanoate.

13. A hair cosmetic composition comprising the following components (A) and (E), (A) 0.2 to 10% by weight of one or more compounds of the following formula (1),

wherein $R^1$ is a methyl or ethyl group, n is an integer of 4–16, and $R^2$ is the following group (i), (ii), or (iii), —$OR^3$      (i)

wherein $R^3$ is a cation selected from the group consisting of alkali metals, alkaline earth metals, ammonium ion, and organic ammonium ions; a hydrogen atom; or an alkyl or alkenyl group having 1–6 carbon atoms,

wherein $R^4$ and $R^5$ individually represents a hydrogen atom, or a $C_{1-6}$ alkyl or alkenyl group which may be substituted or unsubstituted by a hydroxy group, or

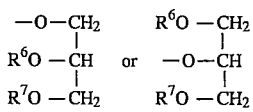  (iii)

wherein $R^6$ and $R^7$ individually represents a hydrogen atom, an alkyl, alkenyl, or acyl group having 1–22 carbon atoms, or a group

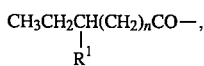

wherein $R^1$ and n have the same meanings as defined above, and (E) 1.0 to 50.0% by weight of one or more monoalkyl ethers of mono- or polyalkylene glycol.

14. The composition of claim 13, wherein component (A) is selected from the group consisting of 18-methyleicosanoic acid, triethanolamine 18-methyleicosanoate, potassium 18-methyleicosanoate, methyl 18-methyleicosanoate, 18-methyleicosanoate ethylamide, potassium 16-methyloctadecanoate, and 2,3-dihydroxypropyl 18-methyleicosanoate.

15. The composition of claim 13, wherein component (A) is triethanolamine 18-methyleicosanoate.

16. A hair cosmetic composition comprising the following components (A), (B), and (C), (A) 0.2 to 10% by weight of one or more compounds of the following formula (1), $$CH_3CH_2CH(CH_2)_nCOR^2 \quad (1)$$
$$\underset{R^1}{|}$$

wherein $R^1$ is a methyl or ethyl group, n is an integer of 4–16, and $R^2$ is the following group (i), (ii), or (iii), —$OR^3$ (i)

wherein $R^3$ is a cation selected from the group consisting of alkali metals, alkaline earth metals, ammonium ion, and organic ammonium ions; a hydrogen atom; or an alkyl or alkenyl group having 1–6 carbon atoms,

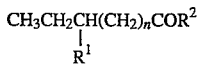  (ii)

wherein $R^4$ and $R^5$ individually represents a hydrogen atom, or a $C_{1-6}$ alkyl or alkenyl group which may be substituted or unsubstituted by a hydroxy group, or

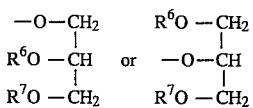  (iii)

wherein $R^6$ and $R^7$ individually represents a hydrogen atom, an alkyl, alkenyl, or acyl group having 1–22 carbon atoms, or a group

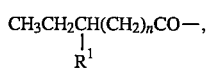

wherein $R^1$ and n have the same meanings as defined above, (B) 0.01 to 40.0% by weight of one or more cationic surface active agents, and (C) 0.05 to 20% by weight of one or more cationic polymers.

17. The composition of claim 16, wherein component (A) is selected from the group consisting of 18-methyleicosanoic acid, triethanolamine 18-methyleicosanoate, potassium 18-methyleicosanoate, methyl 18-methyleicosanoate, 18-methyleicosanoate ethylamide, potassium 16-methyloctadecanoate, and 2,3-dihydroxypropyl 18-methyleicosanoate.

18. The composition of claim 16, wherein component (A) is triethanolamine 18-methyleicosanoate.

19. A hair cosmetic composition comprising the following components (A), (B), and (D), (A) 0.2 to 10% by weight of one or more compounds of the following formula (1),

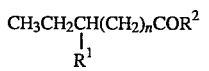  (1)

wherein $R^1$ is a methyl or ethyl group, n is an integer of 4–16, and $R^2$ is the following group (i), (ii), or (iii), —$OR^3$ (i)

wherein $R^3$ is a cation selected from the group consisting of alkali metals, alkaline earth metals, ammonium ion, and organic ammonium ions; a hydrogen atom; or an alkyl or alkenyl group having 1–6 carbon atoms,

  (ii)

wherein $R^4$ and $R^5$ individually represents a hydrogen atom, or a $C_{1-6}$ alkyl or alkenyl group which may be substituted or unsubstituted by a hydroxy group, or

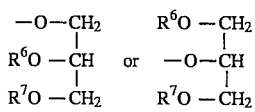  (iii)

wherein $R^6$ and $R^7$ individually represents a hydrogen atom, an alkyl, alkenyl, or acyl group having 1–22 carbon atoms, or a group

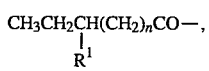

wherein $R^1$ and n have the same meanings as defined above, (B) 0.01 to 40.0% by weight of one or more cationic surface active agents, and (D) 0.01 to 20.0% by weight of one or more silicone compounds.

20. The composition of claim 19, wherein component (A) is selected from the group consisting of 18-methyleicosanoic acid, triethanolamine 18-methyleicosanoate, potassium 18-methyleicosanoate, methyl 18-methyleicosanoate, 18-methyleicosanoate ethylamide, potassium 16-methyloctadecanoate, and 2,3-dihydroxypropyl 18-methyleicosanoate.

21. The composition of claim 19, wherein component (A) is triethanolamine 18-methyleicosanoate.

22. A hair cosmetic composition comprising the following components (A), (B), and (E), (A) 0.2 to 10% by weight of one or more compounds of the following formula (1), $$CH_3CH_2CH(CH_2)_nCOR^2 \atop R^1 \qquad (1)$$

wherein $R^1$ is a methyl or ethyl group, n is an integer of 4–16, and $R^2$ is the following group (i), (ii), or (iii), $$-OR^3 \qquad (i)$$

wherein $R^3$ is a cation selected from the group consisting of alkali metals, alkaline earth metals, ammonium ion, and organic ammonium ions; a hydrogen atom; or an alkyl or alkenyl group having 1–6 carbon atoms,

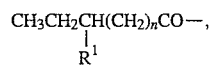

wherein $R^4$ and $R^5$ individually represents a hydrogen atom, or a $C_{1-6}$ alkyl or alkenyl group which may be substituted or unsubstituted by a hydroxy group, or

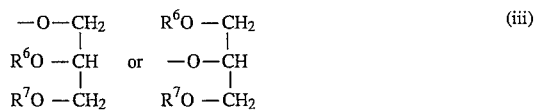

wherein $R^6$ and $R^7$ individually represents a hydrogen atom, an alkyl, alkenyl, or acyl group having 1–22 carbon atoms, or a group $$CH_3CH_2CH(CH_2)_nCO-, \atop R^1$$

wherein $R^1$ and n have the same meanings as defined above, (B) 0.01 to 40.0% by weight of one or more cationic surface active agents, and (E) 1.0 to 50.0% by weight of one or more monoalkyl ethers of mono- or polyalkylene glycol.

23. The composition of claim 22, wherein component (A) is selected from the group consisting of 18-methyleicosanoic acid, triethanolamine 18-methyleicosanoate, potassium 18-methyleicosanoate, methyl 18-methyleicosanoate, 18-methyleicosanoate ethylamide, potassium 16-methyloctadecanoate, and 2,3-dihydroxypropyl 18-methyleicosanoate.

24. The composition of claim 22, wherein component (A) is triethanolamine 18-methyleicosanoate.

* * * * *